United States Patent [19]
Aramayo

[11] 4,230,128
[45] Oct. 28, 1980

[54] CATHETER ATTACHMENT FOR BLOOD SAMPLING

[76] Inventor: Rene S. Aramayo, 3209 N. Military Rd., Arlington, Va. 22207

[21] Appl. No.: 891,888

[22] Filed: Mar. 30, 1978

[51] Int. Cl.² ............................................. A61B 10/00
[52] U.S. Cl. ................................ 128/763; 128/214 R; 128/274; 137/244
[58] Field of Search .............. 128/274, 214 R, 214 B, 128/276, 214.2, 214.4, 2 F, DIG. 5, 1 R; 137/244

[56] References Cited

U.S. PATENT DOCUMENTS

| | | | |
|---|---|---|---|
| 3,459,176 | 8/1969 | Leonard | 128/2 F |
| 3,547,119 | 12/1970 | Hall et al. | 128/214.4 |
| 3,675,891 | 7/1972 | Reynolds et al. | 251/117 |
| 3,727,602 | 4/1973 | Hyden et al. | 128/2 B |
| 3,757,771 | 9/1973 | Ruegg et al. | 128/214.4 |
| 3,774,604 | 11/1973 | Danielsson | 128/274 |

FOREIGN PATENT DOCUMENTS

| | | | |
|---|---|---|---|
| 279951 | 11/1930 | Italy | 137/244 |
| 1024410 | 3/1966 | United Kingdom | 128/214.4 |

*Primary Examiner*—Robert W. Michell
*Assistant Examiner*—J. Kruter
*Attorney, Agent, or Firm*—Millen & White

[57] ABSTRACT

A catheter attachment to be utilized in conjunction with an arterial catheter for blood sampling purposes is disclosed. The attachment includes a housing adapted to be fixedly secured to the catheter, and a stopcock operatively connected to the housing for controlling the flow of blood to a sampling syringe. A sealing stylet is also disposed within the housing in a reciprocal manner so as to be axially inserted within, or withdrawn from, the catheter during non-sampling and sampling periods. In order to insure the disposition of the stylet within the catheter during non-sampling periods, a locking mechanism is also provided which prevents the axial displacement or withdrawal of the stylet from the catheter.

6 Claims, 11 Drawing Figures

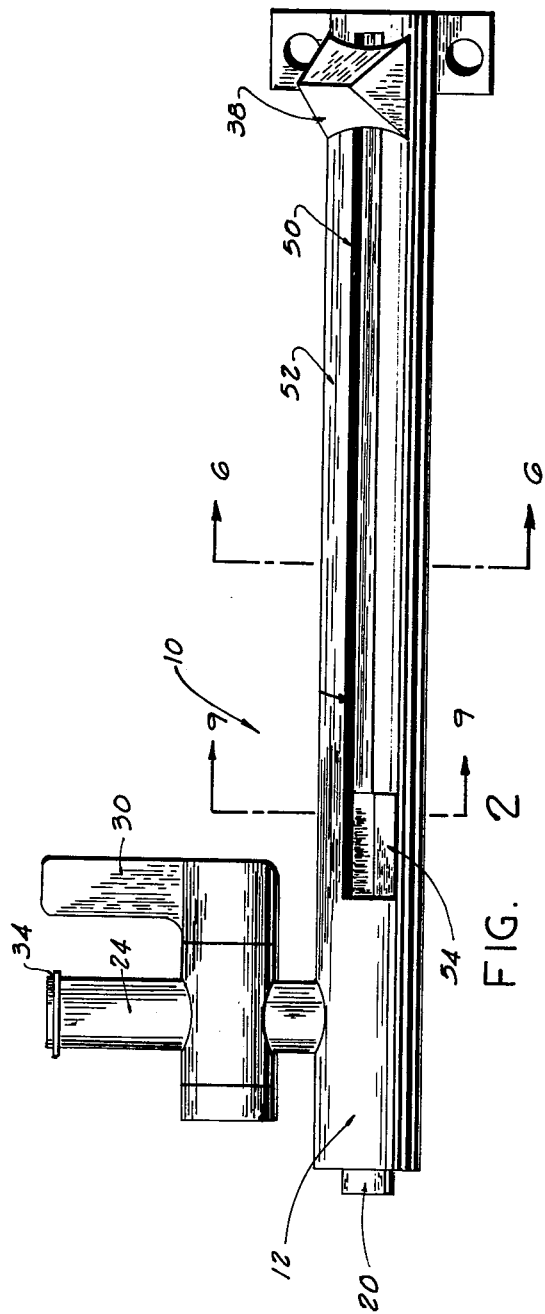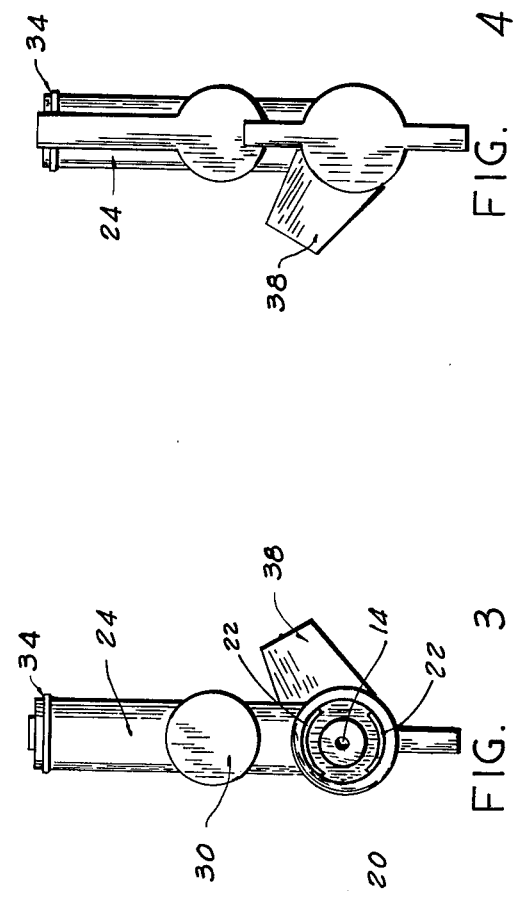

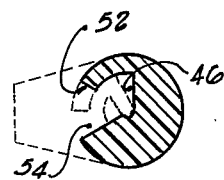
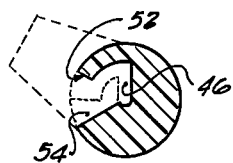
FIG. 9    FIG. 10
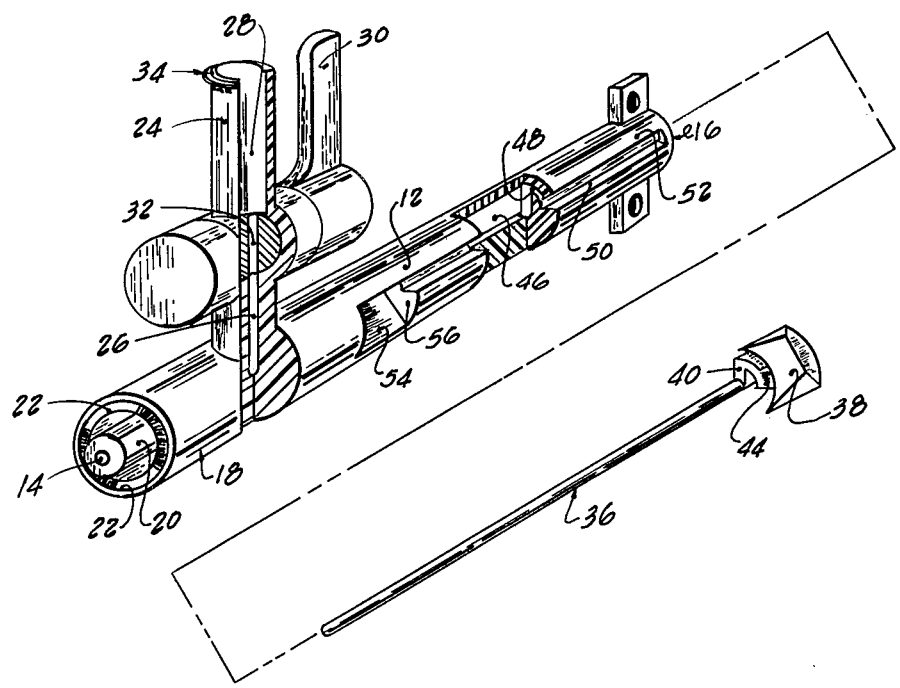
FIG. 11

CATHETER ATTACHMENT FOR BLOOD SAMPLING

FIELD OF THE INVENTION

The present invention relates generally to catheter assemblies, and more particularly to an attachment to be utilized in conjunction with a conventional catheter whereby the procedure of, for example, taking multiple blood samples is considerably expedited and simplified.

BACKGROUND OF THE INVENTION

With reference being initially made to FIG. 1 of the drawings, apparatus conventionally employed in taking blood samples from a patient's artery is shown. More particularly, a flexible plastic catheter 1, which is adapted to removably house a needle cannula 2 when axially disposed therein, is adapted to be inserted within the patient's artery. As is conventional, the proximal end of the needle cannula projects beyond the proximal end of the catheter 1 to permit the puncturing of the artery wall with the cannula while housed in the catheter. The proximal end 3 of the catheter 1 is tapered inwardly toward the proximate end of the cannula so as to facilitate the entry of the catheter into the artery wall aperture formed by the needle cannula.

The distal end of the catheter 1 has a fitting 4 fixedly secured thereto. As is known, the fitting has an axially extending aperture, not shown, so as to fluidically communicate with catheter 1. The head of the fitting 4 has a bead 5 which is adapted to threadedly mate with an internally threaded cap of a sealing stylet (not shown), or alternatively, with an internally threaded tubular end portion of a syringe (not shown).

In a well known manner, when it is desired to take multiple blood samples from a patient, the catheter-cannula assembly is initially inserted into the patient's artery, and subsequently, the needle cannula is removed from the catheter with the latter remaining within the patient's artery. In the instance that a blood sample is in fact ready to be taken, the syringe must be immediately attached to the catheter fitting 4 in order to prevent a substantial amount of blood from issuing out of the catheter. When the desired amount of blood has been deposited within the syringe, the same is disengaged from catheter fitting 4, and a sealing stylet is immediately axially inserted within catheter 1 so as to again prevent blood from issuing out of catheter 1. When another blood sample is desired, the stylet is removed from catheter 1, and in order to prevent a substantial amount of blood from issuing out of catheter 1, a new syringe must immediately be engaged with catheter fitting 4.

As can be readily appreciated from the foregoing description of a conventional blood sampling procedure, the same is quite harried and somewhat difficult to perform in accordance with clinically accepted practices. A need therefore exists for the development of apparatus which will substantially simplify blood sampling procedures and render the same more immaculate.

OBJECTS OF THE INVENTION

Accordingly, it is an object of the present invention to provide a new and improved catheter attachment which will facilitate multiple blood sampling procedures.

Another object of the present invention is to provide a new and improved catheter attachment which will overcome the various disadvantages of prior art devices utilized in conjunction with catheters in accomplishing blood sampling procedures.

Still another object of the present invention is to provide a new and improved catheter attachment which, once engaged with the catheter, permits blood sampling to be performed in a relatively simplified manner.

Yet another object of the present invention is to provide a new and improved catheter attachment which, once engaged with the catheter, permits blood sampling to be performed under virtually immaculate conditons.

A further object of the present invention is to provide a new and improved catheter attachment which, once engaged with the catheter, permits blood sampling to be performed in a completely controlled manner.

A still further object of the present invention is to provide a new and improved catheter attachment which, once engaged with the catheter, permits blood sampling to be performed in an expeditious and efficient manner.

A yet further object of the present invention is to provide a new and improved catheter attachment which is simplistic in construction and relatively inexpensive to manufacture.

SUMMARY OF THE INVENTION

The foregoing and other objectives are achieved in accordance with the present invention through the provision of a catheter attachment which comprises a housing adapted to be lockingly engaged with a catheter fitting. A stopcock is operatively mounted within the housing so as to control the supply of blood from the catheter and the attachment housing to a syringe for sampling purposes, and a sealing stylet is reciprocatingly disposed within the housing so as to be axially inserted within the catheter or withdrawn therefrom curing non-sampling or sampling periods. During non-sampling periods, the disposition of the stylet within the catheter prevents the occurrence of blood clotting therewithin, and in order to insure the presence of the stylet within the catheter during such periods, locking means is provided which prevents the axial displacement or withdrawal of the stylet from the catheter.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 2 is a side elevation view of a catheter attachment constructed in accordance with the present invention and showing its cooperative parts;

FIG. 3 is a front elevation view of the apparatus of FIG. 2;

FIG. 4 is a rear elevation view of the apparatus of FIG. 2;

FIG. 9 is a cross-sectional view of the apparatus of FIG. 2 as taken along the line 9—9 and with the stylet disposed in its locked position;

FIG. 10 is a view similar to that of FIG. 9 with the stylet disposed in its non-locked position; and FIG. 11 is an exploded perspective view of the apparatus of FIG. 2.

DETAILED DESCRIPTION OF THE PREFERRED EMBODIMENT

Figures 1, 5, 6, 7, 8:
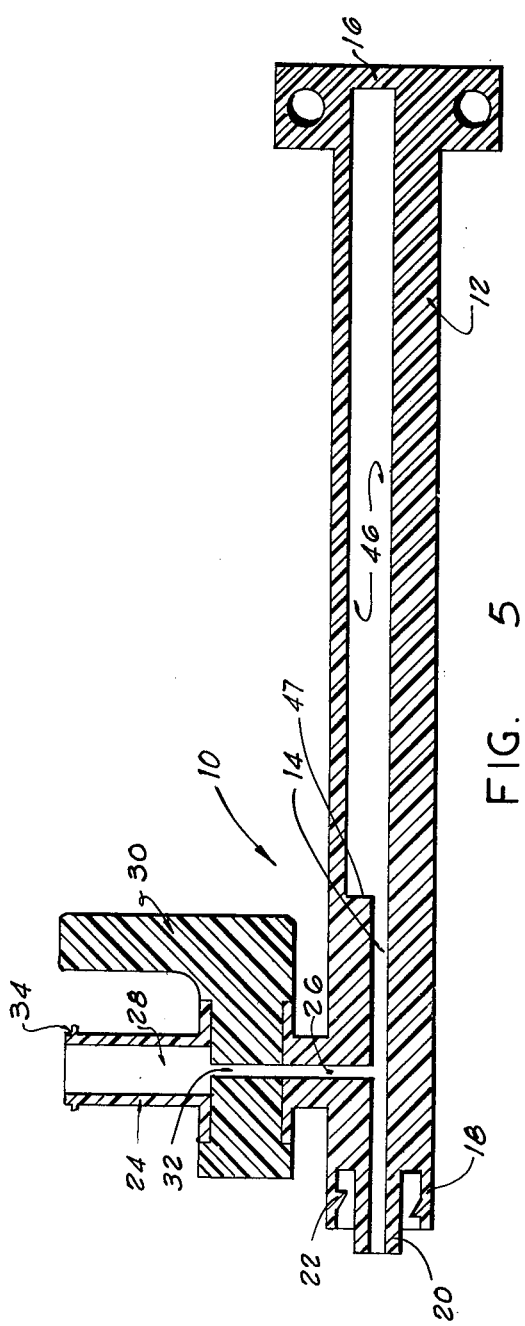
FIG. 1 is an exploded side elevation view of conventional apparatus utilized in performing conventional blood sampling procedures.
FIG. 5 is a longitudinal cross-sectional view of the apparatus of FIG. 2.
FIG. 6 is a lateral cross-sectional view of the apparatus of FIG. 2 as taken along the line 6—6 of FIG. 2.
FIG. 7 is a side elevation view of the stylet of the present invention.
FIG. 8 is a rear elevation view of the stylet of FIG. 7.

Referring again to the drawings, and more particularly to FIGS. 2, 5 and 11 thereof, the catheter attachment of the present invention is generally indicated by the reference character 10 and is seen to comprise a rod-type housing 12 having an axial passageway 14 defined therein. The proximal end of passageway 14 is open while the distal end thereof is closed by means of the housing end wall 16. The proximal end of the housing 12 is provided with an axially extending annular wall 18, and an axial extension 20 which projects beyond wall 18 and within which axial passageway 14 is defined. Annular wall 18 is internally threaded as indicated at 22, and in this manner, when axial projection 20 is inserted into the fitting 4 of a catheter 1, as shown in FIG. 1, threads 22 of housing 12 will lockingly engage the catheter fitting bead 5.

A radially extending tubular fitting 24 is integrally formed with housing 12 within the vicinity of the proximal end thereof, and it is seen that the lower portion of fitting 24 is provided with a fluid passageway 26 which is fluidically connected to axial passageway 14. The upper portion of fitting 24 is similarly provided with a fluid passageway 28, and it is noted that the diametrical extent of passageway 26 is substantially the same as that of axial passageway 14 while the diametrical extent of passageway 28 is somewhat greater. A two-position stop-cock 30 is rotatably mounted within the central portion of fitting 24 and is provided with a diametrically extending fluid passageway 32. The upper end of fitting 24 is externally threaded, as indicated at 34, so as to fixedly mount a syringe (not shown) through means of its tubular portion, and in this manner, depending upon the selected rotary position of stop-cock 30, fluid communication between axial and radial passageways 14 and 26, and radial passageway 28 and the syringe will either be prevented or permitted.

As best seen in FIGS. 5-8 and 11, a stylet 36 is adapted to be slidably disposed within axial passageway 14 in a reciprocal manner. In order to facilitate the reciprocal operation of stylet 36, the same is provided with a handle 38 at the distal end thereof. As the stylet 36 is adapted to periodically be inserted within the catheter 1 in a manner similar to the insertion of a sealing stylet, it is quite important that sterile conditions be maintained as far as is possible with respect to stylet 36. In view of this goal, the means integrally connecting stylet 36 and its handle 38 comprises a thin, radially projecting wall portion 40 integrally connected to stylet 36, an intermediate arcuate-shaped connecting member 42, and a neck 44 integrally connected to handle 38.

In order to accommodate the stylet assembly within housing 12 such that the stylet 36 is disposed within axial passageway 14 while handle 38 projects outwardly from the housing 12 in order to facilitate the manipulation of the stylet, the housing has internal wall structure which is configured similar to the stylet components. More particularly, housing 12 is provided with a radially disposed slot or bore 46, the radially inner portion of which is connected to passageway 14 as best seen in FIG. 6. Bore 46 also extends axially from end wall 16 to an axial position defined by an offset wall portion 47 which is located within the vicinity of the distal end of stop-cock 30. The housing is further provided with an arcuately-shaped, axially extending passageway 48, for accommodating arcuate member 42 of the stylet assembly, as well as a radially disposed, axially extending slot 50 which accommodates the stylet neck 44.

The length of passageway 48 and slot 50 corresponds to that of bore 46, and in this manner, the stylet handle structure may be moved between its extreme positions as dictated by end wall 16 and offset wall 47 so as to correspondingly position stylet 36. As housing 12 is fabricated of a suitable plastic material, and as the thickness of the arcuate wall portion 52 of housing 12, which defines arcuate passageway 48, is quite small, as is the thickness of slot 50, the cooperating structure defined by stylet neck 44, slot 50 and housing wall 52 is such that as neck 44 passes along slot 50, housing wall 52 is resiliently deformed. Slot 50 is normally substantially closed and is only open a substantial degree within the vicinity of handle 38 as dictated by the presence of neck 44. Consequently, the self-closing feature of the aforenoted cooperating structure facilitates the maintenance of sterile conditions with respect to stylet 36.

It is to be noted further that the length of stylet 36 is such that when the stylet assembly is moved to its extreme distal position, the proximal end of stylet 36 will be disposed within that portion of axial passageway 14 defined between fluid passageway 26 and offset wall portion 47. In this manner, the stylet has been removed from the patient's catheter and the blood from the patient is permitted to enter fluid passageway 26. In addition, if stop-cock 30 has been rotated to such a position that its fluid passageway 32 is axially aligned with passageways 26 and 28, then the blood is permitted to enter the syringe 7 for blood sampling purposes. Upon completion of the sampling procedure, stop-cock 30 is rotated so as to terminate the fluid flow from passageway 26 into passageway 28, the sampled syringe is removed, and a new syringe may be mounted upon fitting 24. Upon engagement of the new syringe with fitting 24, the stop-cock may again be rotated to its OPEN position whereby another blood sample may be taken as described hereinbefore.

When the entire blood sampling procedure is to be terminated for a considerable period of time, the stopcock 30 is closed and the last syringe is removed from fitting 24. The stylet assembly is then moved to its proximal extreme position at which the stylet handle structure abuts offset wall 47. The length of stylet 36 is also such that when the assembly is disposed in its proximal position, the proximal end of the stylet 36 is disposed within the vicinity of the proximal end of catheter 1 without the end of the stylet projecting outwardly therefrom and into the patient's artery. In this manner, the stylet prevents any blood from the artery from entering the catheter attachment or the catheter per se whereby the same could tend to clot under stagnant, non-flowing conditions. In conjunction with such procedures, even in the instance that a series of blood samples are to be taken, if the time period between each sample is considerable for one reason or another, then the stylet may also be re-inserted into the catheter during the actual non-sampling periods, and subsequently withdrawn therefrom for sampling purposes, in order to positively insure that clotting or other problems do not occur.

In order to prevent the stylet from becoming disengaged from its extreme proximal position so as to positively prevent accidental clotting or other complications from occurring, housing 12 is also provided with a generally radially defined cut-out portion 54 which is connected to bore 46. As a result of the provision of portion 54, the remaining portion of the housing 12 serves to define a locking shoulder 56 at the distal side of portion 54. In this manner, when the stylet assembly is moved to its extreme proximal position, neck 44 is able to pass beyond shoulder 56 and into the area defined by cut-out section 54. As a result, the stylet structure may be rotated downwardly about the axis defined by stylet 36 and passageway 14 such that neck 44 is now located within the plane of shoulder 56. Consequently, the stylet structure cannot be moved back to its distal position without the same being initially rotated upwardly so as to permit neck 44 to clear shoulder 56. These features are best appreciated as a result of reference being made to FIGS. 9-11.

Thus, it may be seen that the catheter apparatus of the present invention has important advantages over known prior art apparatus due to the fact that when, for example, taking multiple blood samples, once the catheter apparatus of the present invention is engaged with the patient's catheter, the blood samples may be taken in a simplified, controlled manner as the procedure is simplistically controlled by means of the stop-cock and the reciprocal positioning of the stylet structure.

Obviously, many modifications and variations of the present invention are possible in light of the above teachings. It is to be understood therefore that within the scope of the appended claims, the present invention may be practiced otherwise than as specifically described herein.

What is claimed is:

1. An attachment to be utilized in conjunction with a catheter and syringe, comprising: housing means, adapted to be fixedly secured to a catheter, comprising a housing wall formed as a thin-walled structure and fabricated of a resilient plastic material and fluid flow passageway means for fluidically connecting said housing means with a catheter when secured thereto; mounting means on said housing, adapted for mounting a syringe thereon and providing fluid connection therewith with said fluid flow passageway means; a sealing stylet reciprocatively disposed within said housing between two extreme positions for periodically blocking the flow of fluid through said fluid flow passageway means, said fluid flow to said housing being blocked when said stylet is disposed in said first position, and said fluid being permitted to flow to said housing and said mounting means when said stylet is disposed in said second position; handle means for manipulating said stylet between said two extreme positions; a control means for periodically blocking the flow of fluid from said fluid flow passageway means through said mounting means; and means for maintaining said stylet substantially sterile comprising normally closed slot means defined within said housing wall through which said means for manipulating said stylet projects; whereby said slot means is substantially closed, except within the immediate vicinity of said handle means, so as to maintain the interior of said housing substantially sterile.

2. The attachment as set forth in claim 1, wherein: said second control means is a stopcock disposed within said mounting means.

3. The attachment as set forth in claim 1, further comprising: means for locking said sealing stylet in said first extreme position.

4. The attachment as set forth in claim 3, wherein said locking means comprises: shoulder means defined upon said housing; and means defined upon said sealing stylet for engaging said shoulder means.

5. The attachment as set forth in claim 4, further comprising: cut-out means defined within said housing and operatively associated with said shoulder means; and said sealing stylet means is rotatable into and out of said cut-out means for operatively engaging or disengaging said shoulder means.

6. The attachment as set forth in claim 1, wherein: said housing means is elongate and substantially cylindrical; said fluid flow passage means is an axial conduit; said sealing stylet is reciprocatingly axially disposed within said conduit.

* * * * *